US008168866B2

(12) United States Patent
Lightner et al.

(10) Patent No.: US 8,168,866 B2
(45) Date of Patent: *May 1, 2012

(54) GENERATION OF PLANTS WITH ALTERED OIL CONTENT

(75) Inventors: Jonathan Lightner, Des Moines, IA (US); Hein Tsoeng (Medard) Ng, Charlottesville, VA (US); John P. Davies, Portland, OR (US)

(73) Assignee: Agrinomics LLC, South San Francisco, CA (US)

( * ) Notice: Subject to any disclaimer, the term of this patent is extended or adjusted under 35 U.S.C. 154(b) by 349 days.

This patent is subject to a terminal disclaimer.

(21) Appl. No.: 12/427,594

(22) Filed: Apr. 21, 2009

(65) Prior Publication Data

US 2009/0208632 A1 Aug. 20, 2009

Related U.S. Application Data

(63) Continuation of application No. 10/583,199, filed as application No. PCT/US2004/042749 on Dec. 17, 2004, now Pat. No. 7,541,516.

(60) Provisional application No. 60/530,878, filed on Dec. 17, 2003.

(51) Int. Cl.
*A01H 5/00* (2006.01)
*C12N 15/82* (2006.01)
(52) U.S. Cl. ........................................ 800/298; 800/281
(58) Field of Classification Search .................... None
See application file for complete search history.

(56) References Cited

U.S. PATENT DOCUMENTS

| | | | |
|---|---|---|---|
| 5,639,790 A | 6/1997 | Voelker et al. | |
| 5,704,160 A | 1/1998 | Bergquist et al. | |
| 6,229,033 B1 | 5/2001 | Knowlton | |
| 6,248,939 B1 | 6/2001 | Leto et al. | |
| 7,541,516 B2 * | 6/2009 | Lightner et al. | 800/281 |

FOREIGN PATENT DOCUMENTS

| | | |
|---|---|---|
| EP | 1033405 A2 | 2/2000 |
| WO | WO 01/83697 | 8/2001 |

OTHER PUBLICATIONS

Anoop et al., "Modulation of citrate metabolism alters aluminum tolerance in yeast and transgenic canola overexpressing a mitochondrial citrate synthase," *Plant Physiol.*, 132:2205-2217, 2003.
Beisson et al., "*Arabidopsis* genes involved in acyl lipid metabolism. A 2003 census of the candidates, a study of the distribution of expressed sequence tags in organs, and a web-based database," *Plant Physiol.*, 132:681-697, 2003.
Bert et al., "Comparative genetic analysis of quantitative traits in sunflower (*Helianthus annuus* L.). 2. Characterisation of QTL involved in developmental and agronomic traits," *Theor. Appl. Genet.*, 107:181-189, 2003.

Bork et al., "Go hunting in sequence databases but watch out for the traps," *TIG*, 12:425-427, 1996.
Broun et al., "Catalytic Plasticity of Fatty Acid Modification Enzymes Underlying Chemical Diversity of Plant Lipids," *Science*, 282:1315-1317, 1998.
Colbert et al., "High-throughput screening for induced point mutations," *Plant Physiol.*, 126(2):480-484, 2001.
Dehesh et al., "Overexpression of 3-ketoacyl-acyl-carrier protein synthase IIIs in plants reduces the rate of lipid synthesis," *Plant Physiol.*, 125:1103-1114, 2001.
Doerks et al., "Protein annotation: detective work for function prediction," *TIG*, 14(6):248-250, 1998.
Eastmond and Graham, "Re-examining the role of glyoxylate cycle in oilseeds," *Trends Plant Sci.*, 6(2):72-77, 2001.
Eccleston and Ohlrogge, "Expressions of lauroyl-acyl carrier protein thioesterase in *Brassica napus* seeds induces pathways for both fatty acid oxidation and biosynthesis and implies a set point for triacylglycerol accumulation," *Plant Cell.* 10:613-621, 1998.
Fatland et al., "Molecular biology of cytosolic acetyl-CoA generation," *Biochem. Soc. Trans.*, 28(6):593-595, 2000.
Fatland et al., "Reverse genetic characterization of cytosolic acetyl-CoA generation by ATP-citrate lyase in *Arabidopsis*," *Plant Cell*, 17:182-203, 2005.
Feldmann et al., "A Dwarf Mutant of *Arabidopsis* Generated by T-DNA Insertion Mutagenesis," *Science*, 243(4896):1351-1354, 1989.
Focks and Benning, "*wrinkled1*: A novel, low-seed-oil mutant of *Arabidopsis* with a deficiency in the seed-specific regulation of carbohydrate metabolism," *Plant Physiol.*, 118:91-101, 1998.
Girke et al., "Microarray analysis of developing *Arabidopsis* seeds," *Plant Physiol.*, 124:1570-1581, 2000.
Guo et al., "Protein tolerance to random amino acid change," *PNAS*, 101(25):9205-9210, 2004.
Heisler et al., "SPATULA, a gene that controls development of carpel margin tissues in *Arabidopsis*, encodes a bHLH protein" *Development*, 128(7):1089-1098, 2001.
Huq and Quail, "PIF4, a phytochrome-interacting bHLH factor, functions as a negative regulator of phytochrome B signaling in *Arabidopsis*," *EMBO J.*, 21(10):2441-2450, 2002.
Jako et al., "Seed-specific over-expression of an *Arabidopsis* cDNA encoding a diacylglycerol acyltransferase enhances seed oil content and seed weight," *Plant Physiol.*, 126(2):861-874, 2001.
James, D. W. and Dooner, H. K., "Isolation of EMS-induced mutants in *Arabidopsis* altered in seed fatty acid composition," *Theor. Appl. Genet.*, 80(2):241-245, 1990. Katavic et al., "Alteration of seed fatty acid composition by an ethyl methanesulfonate-induced mutation in *Arabidopsis thaliana* affecting diacylglycerol acyltransferase activity," *Plant Physiol.*, 108:399-409, 1995.
Katavic et al., "Utility of the *Arabidopsis FAE1* and yeast *SLC1-1* genes for improvements in erucic acid and oil content in rapeseed," *Biochem Soc. Trans.*, 28(6):935-937, 2000.
Keskin et al., "A new, structurally nonredundant, diverse data set of protein-prtein interfaces and its implications," *Protein Science*, 13:1043-1055, 2004.
Larson et al., "Acyl CoA profiles of transgenic plants that accumulate medium-chain fatty acids indicate inefficient storage lipid synthesis in developing oilseeds," *Plant J.*, 32:519-527, 2002.
Lemieux et al., "Mutants of *Arabidopsis* with alterations in seed lipid fatty acid composition," *Theor. Appl. Genet.*, 80(2):234-240, 1990.

(Continued)

*Primary Examiner* — Elizabeth McElwain
(74) *Attorney, Agent, or Firm* — Klarquist Sparkman, LLP.

(57) ABSTRACT

The present invention is directed to plants that display an altered oil content phenotype due to altered expression of a HIO32.2 nucleic acid. The invention is further directed to methods of generating plants with an altered oil content phenotype.

15 Claims, No Drawings

OTHER PUBLICATIONS

Lin et al., "The Pex16p homolog SSE1 and storage organelle formation in *Arabidopsis* seeds," *Science*. 284:328-330, 1999.

Lionneton et al., "Development of an AFLP-based linkage map and localization of QTLs for seed fatty acid content in condiment mustard (*Brassica juncea*)," *Genome*, 45(6):1203-1215, 2002.

Littlewood and Evan, "Transcription factors 2: helix-loop-helix," *Protein Profile*, 2(6):621-702, 1995.

Liu and Butow, "A transcriptional switch in the expression of yeast tricarboxylic acid cycle genes in response to a reduction or loss of respiratory function," *Mol. Cell. Biol.*, 19:6720-6728, 1999.

McCallum et al., "Targeted screening for induced mutations," *Nat. Biotechnol.*, 18(4):455-457, 2000.

Mekhedov et al., "Toward a functional catalog of the plant genome. A survey of genes for lipid biosynthesis," *Plant Physiol.*, 122:389-401, 2000.

Moire et al., "Impact of unusual fatty acid synthesis on futile cycling through β-oxidation and on gene expression in transgenic plants," *Plant Physiol.*, 134:432-442, 2004.

Neuhaus and Emes, "Nonphotosynthetic Metabolism in Plastids," *Annu. Rev. Plant Physiol. Plant Mol. Biol.*, 51:111-140, 2000.

Ngo et al., "Computational Complexity, Protein Structure Prediction and the Levinthal Paradox," *The Protein Folding Problem and Tertiary Structure Prediction*, K. Merz and S. Le Grand (eds.), 492-495, 1994.

O'Hara et al., "Fatty acid and lipid biosynthetic genes are expressed at constant molar ratios but different absolute levels during embryogenesis," *Plant Physiol.*, 129:310-320, 2002.

Okuley et al., "*Arabidopsis* FAD2 Gene Encodes the Enzyme That Is Essential for Polyunsaturated Lipid Synthesis," *Plant Cell*, 6:147-158, 1994.

Pritchard et al., "Germination and storage reserve mobilization are regulated independently in *Arabidopsis*," *Plant J.*, 31(5):639-647, 2002.

Rajani and Sundaresan, "The *Arabidopsis* myc/bHLH gene ALCATRAZ enables cell separation in fruit dehiscence," *Curr. Biol.*, 11(24):1914-1922, 2001.

Ramsay et al., "Two basic-helix-genes (MYC-146 and GL3) from *Arabidopsis* can activate anthocyanin biosynthesis in a white-flowered *Matthiola incana* mutant," *Plant Molecular Biology*, 52:679-688, 2003.

Rangasamy and Ratledge, "Compartmentation of ATP:Citrate lyase in plants," *Plant Physiol.*, 122:1225-1230, 2000.

Rangasamy and Ratledge, "Genetic enhancement of fatty acid synthesis by targeting rat liver ATP:citrate lyase into plastids of tobacco," *Plant Physiol.*, 122:1231-1238, 2000.

Ratledge et al, "Correlation of ATP/citrate lyase activity with lipid accumulation in developing seeds of *Brassica napus* L.," *Lipids*, 32(1):7-12, 1997.

Rawsthorne, S., "Carbon flux and fatty acid synthesis in plants," *Prog Lipid Res.*, 41:182-196, 2002.

Ruuska et al., "Contrapuntal networks of gene expression during *Arabidopsis* seed filling," *Plant Cell*, 14:1191-1206, 2002.

Rylott et al., "Co-ordinate regulation of genes involved in storage lipid mobilization in *Arabidopsis thaliana*," *Biochem Soc. Trans.*, 29:283-287, 2001.

Sawa, Shinichiro, "Overexpression of the AtmybL2 gene represses trichome development in *Arabidopsis*," *DNA Res.*, 9(2):31-34, 2002.

Schnarrenberger and Martin, "Evolution of the enzymes of the citric acid cycle and the glyoxylate cycle of higher plants, A case study of endosymbiotic gene transfer," *Eur. J. Biochem.*, 269:868-883, 2002.

Schnurr et al., "Characterization of an acyl-CoA synthetase from *Arabidopsis thaliana*," *Biochem Soc.Trans.*, 28(6):957-958, 2000.

Shockey et al., "Characterization of the AMP-binding protein gene family in *Arabidopsis thaliana*: will the real acyl-CoA synthetases please stand up?" *Biochem Soc. Trans.*, 28(6):955-957, 2000.

Smith et al., "The challenges of genome sequence annotation or 'The devil is in the details'," *Nature Biotechnology*, 15:1222-1223, 1997.

Smolen et al., "Dominant alleles of the basic helix-loop-helix transcription factor ATR2 activate stress-responsive genes in *Arabidopsis*," *Genetics*, 161(3):1235-1246, 2002.

Thelen et al., "Biotin carboxyl carrier protein isoforms in *Brassicaceae* oilseeds," *Biochem. Soc. Trans.*, 28(6):595-598, 2000.

Thornton et al., "From structure to function: Approaches and limitations," *Nature Structural Biology, structural genomics supplement*, (no vol. #):991-994, 2000.

Wada et al., "Role of a positive regulator of root hair development, CAPRICE, in *Arabidopsis* root epidermal cell differentiation," *Development*, 129(23):5409-5419, 2002.

Wells, James A., "Additivity of Mutational Effects in Proteins," *Biochemistry*, 29(37):8509-8517, 1990.

White et al., "A new set of *Arabidopsis* expressed sequence tags from developing seeds. The metabolic pathway from carbohydrates to seed oil," *Plant Physiol.*, 124:1582-1594, 2000.

Yadav et al., "Cloning of higher plant omega-3 fatty acid desaturases," *Plant Physiol.*, 103(2):467-476, 1993.

Zou et al., "Modification of Seed Oil Content and Acyl Composition in the *Brassicaceae* by Expression of a Yeast *sn*-2 Acyltransferase Gene," *The Plant Cell*, 9:909-923, 1997.

Database N Geneseq, Accession No. AAC50547, Oct. 18, 2000.

\* cited by examiner

GENERATION OF PLANTS WITH ALTERED OIL CONTENT

REFERENCE TO RELATED APPLICATIONS

This is the Continuation of application Ser. No. 10/583,199, filed on Jun. 15, 2006, issued as U.S. Pat. No. 7,541,516, on Jun. 2, 2009, which is the §371 U.S. National Stage of International Application No. PCT/US2004/042749, filed on Dec. 17, 2004, which was published in English under PCT Article 21(2), and which in turn claims the benefit of U.S. Provisional Patent Application No. 60/530,878, filed Dec. 17, 2003. All of these applications are hereby incorporated by reference.

BACKGROUND OF THE INVENTION

The ability to manipulate the composition of crop seeds, particularly the content and composition of seed oils, has important applications in the agricultural industries, relating both to processed food oils and to oils for animal feeding. Seeds of agricultural crops contain a variety of valuable constituents, including oil, protein and starch. Industrial processing can separate some or all of these constituents for individual sale in specific applications. For instance, nearly 60% of the U.S. soybean crop is crushed by the soy processing industry. Soy processing yields purified oil, which is sold at high value, while the remainder is sold principally for lower value livestock feed (U.S. Soybean Board, 2001 Soy Stats). Canola seed is crushed to produce oil and the co-product canola meal (Canola Council of Canada). Nearly 20% of the 1999/2000 U.S. corn crop was industrially refined, primarily for production of starch, ethanol and oil (Corn Refiners Association). Thus, it is often desirable to maximize oil content of seeds. For instance, for processed oilseeds such as soy and canola, increasing the absolute oil content of the seed will increase the value of such grains. For processed corn it may be desired to either increase or decrease oil content, depending on utilization of other major constituents. Decreasing oil may improve the quality of isolated starch by reducing undesired flavors associated with oil oxidation. Alternatively, in ethanol production, where flavor is unimportant, increasing oil content may increase overall value. In many fed grains, such as corn and wheat, it is desirable to increase seed oil content, because oil has higher energy content than other seed constituents such as carbohydrate. Oilseed processing, like most grain processing businesses, is a capital-intensive business; thus small shifts in the distribution of products from the low valued components to the high value oil component can have substantial economic impacts for grain processors.

Biotechnological manipulation of oils can provide compositional alteration and improvement of oil yield. Compositional alterations include high oleic soybean and corn oil (U.S. Pat. Nos. 6,229,033 and 6,248,939), and laurate-containing seeds (U.S. Pat. No. 5,639,790), among others. Work in compositional alteration has predominantly focused on processed oilseeds but has been readily extendable to non-oilseed crops, including corn. While there is considerable interest in increasing oil content, the only currently practiced biotechnology in this area is High-Oil Corn (HOC) technology (DuPont, U.S. Pat. No. 5,704,160). HOC employs high oil pollinators developed by classical selection breeding along with elite (male-sterile) hybrid females in a production system referred to as TopCross. The TopCross High Oil system raises harvested grain oil content in maize from about 3.5% to about 7%, improving the energy content of the grain.

While it has been fruitful, the HOC production system has inherent limitations. First, the system of having a low percentage of pollinators responsible for an entire field's seed set contains inherent risks, particularly in drought years. Second, oil contents in current HOC fields have plateaued at about 9% oil. Finally, high-oil corn is not primarily a biochemical change, but rather an anatomical mutant (increased embryo size) that has the indirect result of increasing oil content. For these reasons, an alternative high oil strategy, particularly one that derives from an altered biochemical output, would be especially valuable.

The most obvious target crops for the processed oil market are soy and rapeseed, and a large body of commercial work (e.g., U.S. Pat. No. 5,952,544; PCT application WO9411516) demonstrates that *Arabidopsis* is an excellent model for oil metabolism in these crops. Biochemical screens of seed oil composition have identified *Arabidopsis* genes for many critical biosynthetic enzymes and have led to identification of agronomically important gene orthologs. For instance, screens using chemically mutagenized populations have identified lipid mutants whose seeds display altered fatty acid composition (Lemieux et al., 1990; James and Dooner, 1990). T-DNA mutagenesis screens (Feldmann et al., 1989) that detected altered fatty acid composition identified the omega 3 desaturase (FAD3) and delta-12 desaturase (FAD2) genes (U.S. Pat. No. 5,952,544; Yadav et al., 1993; Okuley et al., 1994). A screen which focused on oil content rather than oil quality, analyzed chemically-induced mutants for wrinkled seeds or altered seed density, from which altered seed oil content was inferred (Focks and Benning, 1998). Another screen, designed to identify enzymes involved in production of very long chain fatty acids, identified a mutation in the gene encoding a diacylglycerol acyltransferase (DGAT) as being responsible for reduced triacyl glycerol accumulation in seeds (Katavic V et al, 1995). It was further shown that seed-specific over-expression of the DGAT cDNA was associated with increased seed oil content (Jako et al., 2001).

Activation tagging in plants refers to a method of generating random mutations by insertion of a heterologous nucleic acid construct comprising regulatory sequences (e.g., an enhancer) into a plant genome. The regulatory sequences can act to enhance transcription of one or more native plant genes; accordingly, activation tagging is a fruitful method for generating gain-of-function, generally dominant mutants (see, e.g., Hayashi et al., 1992; Weigel D et al. 2000). The inserted construct provides a molecular tag for rapid identification of the native plant whose mis-expression causes the mutant phenotype. Activation tagging may also cause loss-of-function phenotypes. The insertion may result in disruption of a native plant gene, in which case the phenotype is generally recessive.

Activation tagging has been used in various species, including tobacco and *Arabidopsis*, to identify many different kinds of mutant phenotypes and the genes associated with these phenotypes (Wilson et al., 1996, Schaffer et al., 1998, Fridborg et al., 1999; Kardailsky et al., 1999; Christensen S et al. 1998).

SUMMARY OF THE INVENTION

The invention provides a transgenic plant having a high oil phenotype. The transgenic plant comprises a transformation vector comprising a nucleotide sequence that encodes or is complementary to a sequence that encodes a HIO32.2 polypeptide comprising the amino acid sequence of SEQ ID NO:2, or an ortholog thereof. In preferred embodiments, the transgenic plant is selected from the group consisting of rapeseed, soy, corn, sunflower, cotton, cocoa, safflower, oil palm, coconut palm, flax, castor and peanut. The invention also provides a method of producing oil comprising growing the transgenic plant and recovering oil from said plant. The invention further provides a method of generating a plant having a high oil phenotype by identifying a plant that has an allele in its HIO32.2 gene that results in increased oil content compared to plants lacking the allele and generating progeny of the identified plant, wherein the generated progeny inherit the allele and have the high oil phenotype.

The transgenic plant of the invention is produced by a method that comprises introducing into progenitor cells of the plant a plant transformation vector comprising a nucleotide sequence that encodes or is complementary to a sequence that encodes a HIO32.2 polypeptide, and growing the transformed progenitor cells to produce a transgenic plant, wherein the HIO32.2 polynucleotide sequence is expressed causing the high oil phenotype.

DETAILED DESCRIPTION OF THE INVENTION

Definitions

Unless otherwise indicated, all technical and scientific terms used herein have the same meaning as they would to one skilled in the art of the present invention. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

As used herein, the term "vector" refers to a nucleic acid construct designed for transfer between different host cells. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art.

A "heterologous" nucleic acid construct or sequence has a portion of the sequence that is not native to the plant cell in which it is expressed. Heterologous, with respect to a control sequence refers to a control sequence (i.e. promoter or enhancer) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. A "heterologous" nucleic acid construct may contain a control sequence/DNA coding sequence combination that is the same as, or different from a control sequence/DNA coding sequence combination found in the native plant.

As used herein, the term "gene" means the segment of DNA involved in producing a polypeptide chain, which may or may not include regions preceding and following the coding region, e.g. 5' untranslated (5' UTR) or "leader" sequences and 3' UTR or "trailer" sequences, as well as intervening sequences (introns) between individual coding segments (exons) and non-transcribed regulatory sequence.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

As used herein, the term "gene expression" refers to the process by which a polypeptide is produced based on the nucleic acid sequence of a gene. The process includes both transcription and translation; accordingly, "expression" may refer to either a polynucleotide or polypeptide sequence, or both. Sometimes, expression of a polynucleotide sequence will not lead to protein translation. "Over-expression" refers to increased expression of a polynucleotide and/or polypeptide sequence relative to its expression in a wild-type (or other reference [e.g., non-transgenic]) plant and may relate to a naturally-occurring or non-naturally occurring sequence. "Ectopic expression" refers to expression at a time, place, and/or increased level that does not naturally occur in the non-altered or wild-type plant. "Under-expression" refers to decreased expression of a polynucleotide and/or polypeptide sequence, generally of an endogenous gene, relative to its expression in a wild-type plant. The terms "mis-expression" and "altered expression" encompass over-expression, under-expression, and ectopic expression.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, a "plant cell" refers to any cell derived from a plant, including cells from undifferentiated tissue (e.g., callus) as well as plant seeds, pollen, progagules and embryos.

As used herein, the terms "native" and "wild-type" relative to a given plant trait or phenotype refers to the form in which that trait or phenotype is found in the same variety of plant in nature.

As used herein, the term "modified" regarding a plant trait, refers to a change in the phenotype of a transgenic plant relative to the similar non-transgenic plant. An "interesting phenotype (trait)" with reference to a transgenic plant refers to an observable or measurable phenotype demonstrated by a T1 and/or subsequent generation plant, which is not displayed by the corresponding non-transgenic (i.e., a genotypically similar plant that has been raised or assayed under similar conditions). An interesting phenotype may represent an improvement in the plant or may provide a means to produce improvements in other plants. An "improvement" is a feature that may enhance the utility of a plant species or variety by providing the plant with a unique and/or novel quality. An "altered oil content phenotype" refers to measurable phenotype of a genetically modified plant, where the plant displays a statistically significant increase or decrease in overall oil content (i.e., the percentage of seed mass that is oil), as compared to the similar, but non-modified plant. A high oil phenotype refers to an increase in overall oil content.

As used herein, a "mutant" polynucleotide sequence or gene differs from the corresponding wild type polynucleotide sequence or gene either in terms of sequence or expression, where the difference contributes to a modified plant phenotype or trait. Relative to a plant or plant line, the term "mutant" refers to a plant or plant line which has a modified plant phenotype or trait, where the modified phenotype or trait is associated with the modified expression of a wild type polynucleotide sequence or gene.

As used herein, the term "T1" refers to the generation of plants from the seed of T0 plants. The T1 generation is the first set of transformed plants that can be selected by application of a selection agent, e.g., an antibiotic or herbicide, for which the transgenic plant contains the corresponding resistance gene. The term "T2" refers to the generation of plants by self-fertilization of the flowers of T1 plants, previously selected as being transgenic. T3 plants are generated from T2 plants, etc. As used herein, the "direct progeny" of a given plant derives from the seed (or, sometimes, other tissue) of that plant and is in the immediately subsequent generation; for instance, for a given lineage, a T2 plant is the direct progeny of a T1 plant. The "indirect progeny" of a given plant derives from the seed (or other tissue) of the direct progeny of that plant, or from the seed (or other tissue) of subsequent generations in that lineage; for instance, a T3 plant is the indirect progeny of a T1 plant.

As used herein, the term "plant part" includes any plant organ or tissue, including, without limitation, seeds, embryos, meristematic regions, callus tissue, leaves, roots, shoots, gametophytes, sporophytes, pollen, and microspores. Plant cells can be obtained from any plant organ or tissue and cultures prepared therefrom. The class of plants which can be used in the methods of the present invention is generally as broad as the class of higher plants amenable to transformation techniques, including both monocotyledenous and dicotyledenous plants.

As used herein, "transgenic plant" includes a plant that comprises within its genome a heterologous polynucleotide. The heterologous polynucleotide can be either stably integrated into the genome, or can be extra-chromosomal. Preferably, the polynucleotide of the present invention is stably integrated into the genome such that the polynucleotide is passed on to successive generations. A plant cell, tissue, organ, or plant into which the heterologous polynucleotides have been introduced is considered "transformed", "transfected", or "transgenic". Direct and indirect progeny of transformed plants or plant cells that also contain the heterologous polynucleotide are also considered transgenic.

Identification of Plants with an Altered Oil Content Phenotype

We used an *Arabidopsis* activation tagging screen to identify the association between the gene we have designated "HIO32.2," (At3g47710; GI#22331644 encoding protein T23J7.40 (GI#22331654), and an altered oil content phenotype (specifically, a high oil phenotype). Briefly, and as further described in the Examples, a large number of *Arabidopsis* plants were mutated by transformation with the pSKI015 vector, which comprises a T-DNA from the Ti plasmid of *Agrobacterium tumifaciens*, a viral enhancer element, and a selectable marker gene (Weigel et al, 2000). When the T-DNA inserts into the genome of transformed plants, the enhancer element can cause up-regulation genes in the vicinity, generally within about 10 kilobase (kb) of the enhancers. To identify transgenic plants, T1 plants were exposed to the selective agent in order to specifically recover transformed plants that expressed the selectable marker and therefore harboring the T-DNA. T2 seed was harvested from these plants. Lipids were extracted from of about 15-20 T2 seeds. Gas chromatography (GC) analysis was performed to determine fatty acid content and composition of seed samples.

An *Arabidopsis* line that showed a high-oil phenotype was identified, wherein oil content (i.e., fatty acids) constituted about 36.3% of seed mass compared to an average oil content of about 27.0% for seed from other plants grown and analyzed at the same time (a 34% in oil). The association of the HIO32.2 gene with the high oil phenotype was discovered by identifying the site of T-DNA insertion, and as shown in the Examples, demonstrating genetic co-segregation of the high seed oil phenotype and the presence of the T-DNA. Accordingly, HIO32.2 genes and/or polypeptides may be employed in the development of genetically modified plants having a modified oil content phenotype ("a HIO32.2 phenotype"). HIO32.2 genes may be used in the generation of oilseed crops that provide improved oil yield from oilseed processing and in the generation of feed grain crops that provide increased energy for animal feeding. HIO32.2 genes may further be used to increase the oil content of specialty oil crops, in order to augment yield of desired unusual fatty acids. Transgenic plants that have been genetically modified to express HIO32.2 can be used in the production of oil, wherein the transgenic plants are grown, and oil is obtained from plant parts (e.g. seed) using standard methods.

HIO32.2 Nucleic Acids and Polypeptides

*Arabidopsis* HIO32.2 nucleic acid (genomic DNA) sequence is provided in SEQ ID NO:1 and in Genbank entry GI#22331644. The corresponding protein sequence is provided in SEQ ID NO:2 and in GI#22331645. Nucleic acids and/or proteins that are orthologs or paralogs of *Arabidopsis* HIO32.2, are described in Example 3 below.

As used herein, the term "HIO32.2 polypeptide" refers to a full-length HIO32.2 protein or a fragment, derivative (variant), or ortholog thereof that is "functionally active," meaning that the protein fragment, derivative, or ortholog exhibits one or more or the functional activities associated with the polypeptide of SEQ ID NO:2. In one preferred embodiment, a functionally active HIO32.2 polypeptide causes an altered oil content phenotype when mis-expressed in a plant. In a further preferred embodiment, mis-expression of the HIO32.2 polypeptide causes a high oil phenotype in a plant. In another embodiment, a functionally active HIO32.2 polypeptide is capable of rescuing defective (including deficient) endogenous HIO32.2 activity when expressed in a plant or in plant cells; the rescuing polypeptide may be from the same or from a different species as that with defective activity. In another embodiment, a functionally active fragment of a full length HIO32.2 polypeptide (i.e., a native polypeptide having the sequence of SEQ ID NO:2 or a naturally occurring ortholog thereof) retains one of more of the biological properties associated with the full-length HIO32.2 polypeptide, such as signaling activity, binding activity, catalytic activity, or cellular or extra-cellular localizing activity. A HIO32.2 fragment preferably comprises a HIO32.2 domain, such as a C- or N-terminal or catalytic domain, among others, and preferably comprises at least 10, preferably at least 20, more preferably at least 25, and most preferably at least 50 contiguous amino acids of a HIO32.2 protein. Functional domains can be identified using the PFAM program (Bateman A et al., 1999 Nucleic Acids Res 27:260-262). A preferred HIO32.2 fragment comprises a helix-loop-helix DNA-binding domain (PF00010). Functionally active variants of full-length HIO32.2 polypeptides or fragments thereof include polypeptides with amino acid insertions, deletions, or substitutions that retain one of more of the biological properties associated with the full-length HIO32.2 polypeptide. In some cases, variants are generated that change the post-translational processing of a HIO32.2 polypeptide. For instance, variants may have altered protein transport or protein localization characteristics or altered protein half-life compared to the native polypeptide.

As used herein, the term "HIO32.2 nucleic acid" encompasses nucleic acids with the sequence provided in or complementary to the sequence provided in SEQ ID NO:1, as well as functionally active fragments, derivatives, or orthologs thereof. A HIO32.2 nucleic acid of this invention may be DNA, derived from genomic DNA or cDNA, or RNA.

In one embodiment, a functionally active HIO32.2 nucleic acid encodes or is complementary to a nucleic acid that encodes a functionally active HIO32.2 polypeptide. Included within this definition is genomic DNA that serves as a template for a primary RNA transcript (i.e., an mRNA precursor) that requires processing, such as splicing, before encoding the functionally active HIO32.2 polypeptide. A HIO32.2 nucleic acid can include other non-coding sequences, which may or may not be transcribed; such sequences include 5' and 3' UTRs, polyadenylation signals and regulatory sequences that control gene expression, among others, as are known in the art. Some polypeptides require processing events, such as proteolytic cleavage, covalent modification, etc., in order to become fully active. Accordingly, functionally active nucleic acids may encode the mature or the pre-processed HIO32.2 polypeptide, or an intermediate form. A HIO32.2 polynucleotide can also include heterologous coding sequences, for example, sequences that encode a marker included to facilitate the purification of the fused polypeptide, or a transformation marker.

In another embodiment, a functionally active HIO32.2 nucleic acid is capable of being used in the generation of loss-of-function HIO32.2 phenotypes, for instance, via antisense suppression, co-suppression, etc.

In one preferred embodiment, a HIO32.2 nucleic acid used in the methods of this invention comprises a nucleic acid sequence that encodes or is complementary to a sequence that encodes a HIO32.2 polypeptide having at least 50%, 60%, 70%, 75%, 80%, 85%, 90%, 95% or more sequence identity to the polypeptide sequence presented in SEQ ID NO:2.

In another embodiment a HIO32.2 polypeptide of the invention comprises a polypeptide sequence with at least 50% or 60% identity to the HIO32.2 polypeptide sequence of SEQ ID NO:2, and may have at least 70%, 80%, 85%, 90% or 95% or more sequence identity to the HIO32.2 polypeptide sequence of SEQ ID NO:2. In another embodiment, a HIO32.2 polypeptide comprises a polypeptide sequence with at least 50%, 60%, 70%, 80%, 85%, 90% or 95% or more sequence identity to a functionally active fragment of the polypeptide presented in SEQ ID NO:2, such as a helix-loop-helix DNA-binding domain. In yet another embodiment, a HIO32.2 polypeptide comprises a polypeptide sequence with at least 50%, 60%, 70%, 80%, or 90% identity to the polypeptide sequence of SEQ ID NO:2 over its entire length and comprises a helix-loop-helix DNA-binding domain.

In another aspect, a HIO32.2 polynucleotide sequence is at least 50% to 60% identical over its entire length to the HIO32.2 nucleic acid sequence presented as SEQ ID NO:1, or nucleic acid sequences that are complementary to such a HIO32.2 sequence, and may comprise at least 70%, 80%, 85%, 90% or 95% or more sequence identity to the HIO32.2 sequence presented as SEQ ID NO:1 or a functionally active fragment thereof, or complementary sequences.

As used herein, "percent (%) sequence identity" with respect to a specified subject sequence, or a specified portion thereof, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1990) 215:403-410) with search parameters set to default values. The HSP S and HSP S2 parameters are dynamic values and are established by the program itself depending upon the composition of the particular sequence and composition of the particular database against which the sequence of interest is being searched. A "% identity value" is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Derivative nucleic acid molecules of the subject nucleic acid molecules include sequences that selectively hybridize to the nucleic acid sequence of SEQ ID NO:1. The stringency of hybridization can be controlled by temperature, ionic strength, pH, and the presence of denaturing agents such as formamide during hybridization and washing. Conditions routinely used are well known (see, e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of SEQ ID NO:1 under stringent hybridization conditions that are: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.1×SSC and 0.1% SDS (sodium dodecyl sulfate). In other embodiments, moderately stringent hybridization conditions are used that are: pretreatment of filters containing nucleic acid for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA; hybridization for 18-20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 µg/ml salmon sperm DNA, and 10% (wt/vol) dextran sulfate; followed by washing twice for 1 hour at 55° C. in a solution containing 2×SSC and 0.1% SDS. Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

As a result of the degeneracy of the genetic code, a number of polynucleotide sequences encoding a HIO32.2 polypeptide can be produced. For example, codons may be selected to increase the rate at which expression of the polypeptide occurs in a particular host species, in accordance with the optimum codon usage dictated by the particular host organism (see, e.g., Nakamura et al, 1999). Such sequence variants may be used in the methods of this invention.

The methods of the invention may use orthologs of the *Arabidopsis* HIO32.2. Methods of identifying the orthologs in other plant species are known in the art. Normally, orthologs in different species retain the same function, due to presence of one or more protein motifs and/or 3-dimensional structures. In evolution, when a gene duplication event follows speciation, a single gene in one species, such as *Arabidopsis*, may correspond to multiple genes (paralogs) in another. As used herein, the term "orthologs" encompasses paralogs. When sequence data is available for a particular plant species, orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. Nucleic acid hybridization methods may also be used to find orthologous genes and are preferred when sequence data are not available. Degenerate PCR and screening of cDNA or genomic DNA libraries are common methods for finding related gene sequences and are well known in the art (see, e.g., Sambrook, 1989; Dieffenbach and Dveksler, 1995). For instance, methods for generating a cDNA library from the plant species of interest and probing the library with partially homologous gene probes are described in Sambrook et al. A highly conserved portion of the *Arabidopsis* HIO32.2 coding sequence may be used as a probe. HIO32.2 ortholog nucleic acids may hybridize to the nucleic acid of SEQ ID NO:1 under high, moderate, or low stringency conditions. After amplification or isolation of a segment of a putative ortholog, that segment may be cloned and sequenced by standard techniques and utilized as a probe to isolate a complete cDNA or genomic clone. Alternatively, it is possible to initiate an EST project to generate a database of sequence information for the plant species of interest. In another approach, antibodies that specifically bind known HIO32.2 polypeptides are used for ortholog isolation (see, e.g., Harlow and Lane, 1988, 1999). Western blot analysis can determine that a HIO32.2 ortholog (i.e., an orthologous protein) is present in a crude extract of a particular plant species. When reactivity is observed, the sequence encoding the candidate ortholog may be isolated by screening expression libraries representing the particular plant species. Expression libraries can be constructed in a variety of commercially available vectors, including lambda gt11, as described in Sambrook, et al., 1989. Once the candidate ortholog(s) are identified by any of these means, candidate orthologous sequence are used as bait (the "query") for the reverse BLAST against sequences from *Arabidopsis* or other species in which HIO32.2 nucleic acid and/or polypeptide sequences have been identified.

HIO32.2 nucleic acids and polypeptides may be obtained using any available method. For instance, techniques for isolating cDNA or genomic DNA sequences of interest by screening DNA libraries or by using polymerase chain reaction (PCR), as previously described, are well known in the art. Alternatively, nucleic acid sequence may be synthesized. Any known method, such as site directed mutagenesis (Kunkel T A et al., 1991), may be used to introduce desired changes into a cloned nucleic acid.

In general, the methods of the invention involve incorporating the desired form of the HIO32.2 nucleic acid into a plant expression vector for transformation of in plant cells, and the HIO32.2 polypeptide is expressed in the host plant.

An isolated HIO32.2 nucleic acid molecule is other than in the form or setting in which it is found in nature and is identified and separated from least one contaminant nucleic acid molecule with which it is ordinarily associated in the natural source of the HIO32.2 nucleic acid. However, an isolated HIO32.2 nucleic acid molecule includes HIO32.2 nucleic acid molecules contained in cells that ordinarily express HIO32.2 where, for example, the nucleic acid molecule is in a chromosomal location different from that of natural cells.

Generation of Genetically Modified Plants with an Altered Oil Content Phenotype

HIO32.2 nucleic acids and polypeptides may be used in the generation of genetically modified plants having a modified oil content phenotype. As used herein, a "modified oil content phenotype" may refer to modified oil content in any part of the plant; the modified oil content is often observed in seeds. In a preferred embodiment, altered expression of the HIO32.2 gene in a plant is used to generate plants with a high oil phenotype.

The methods described herein are generally applicable to all plants. Although activation tagging and gene identification is carried out in *Arabidopsis*, the HIO32.2 gene (or an ortholog, variant or fragment thereof) may be expressed in any type of plant. In a preferred embodiment, the invention is directed to oil-producing plants, which produce and store triacylglycerol in specific organs, primarily in seeds. Such species include soybean (*Glycine max*), rapeseed and canola (including *Brassica napus, B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The invention may also be directed to fruit- and vegetable-bearing plants, grain-producing plants, nut-producing plants, rapid cycling *Brassica* species, alfalfa (*Medicago sativa*), tobacco (Nicotiana), turfgrass (Poaceae family), other forage crops, and wild species that may be a source of unique fatty acids.

The skilled artisan will recognize that a wide variety of transformation techniques exist in the art, and new techniques are continually becoming available. Any technique that is suitable for the target host plant can be employed within the scope of the present invention. For example, the constructs can be introduced in a variety of forms including, but not limited to as a strand of DNA, in a plasmid, or in an artificial chromosome. The introduction of the constructs into the target plant cells can be accomplished by a variety of techniques, including, but not limited to *Agrobacterium*-mediated transformation, electroporation, microinjection, microprojectile bombardment calcium-phosphate-DNA co-precipitation or liposome-mediated transformation of a heterologous nucleic acid. The transformation of the plant is preferably permanent, i.e. by integration of the introduced expression constructs into the host plant genome, so that the introduced constructs are passed onto successive plant generations. Depending upon the intended use, a heterologous nucleic acid construct comprising an HIO32.2 polynucleotide may encode the entire protein or a biologically active portion thereof.

In one embodiment, binary Ti-based vector systems may be used to transfer polynucleotides. Standard *Agrobacterium* binary vectors are known to those of skill in the art, and many are commercially available (e.g., pBI121 Clontech Laboratories, Palo Alto, Calif.).

The optimal procedure for transformation of plants with *Agrobacterium* vectors will vary with the type of plant being transformed. Exemplary methods for *Agrobacterium*-mediated transformation include transformation of explants of hypocotyl, shoot tip, stem or leaf tissue, derived from sterile seedlings and/or plantlets. Such transformed plants may be reproduced sexually, or by cell or tissue culture. *Agrobacterium* transformation has been previously described for a large number of different types of plants and methods for such transformation may be found in the scientific literature. Of particular relevance are methods to transform commercially important crops, such as rapeseed (De Block et al., 1989), sunflower (Everett et al., 1987), and soybean (Christou et al., 1989; Kline et al., 1987).

Expression (including transcription and translation) of HIO32.2 may be regulated with respect to the level of expression, the tissue type(s) where expression takes place and/or developmental stage of expression. A number of heterologous regulatory sequences (e.g., promoters and enhancers) are available for controlling the expression of a HIO32.2 nucleic acid. These include constitutive, inducible and regulatable promoters, as well as promoters and enhancers that control expression in a tissue- or temporal-specific manner. Exemplary constitutive promoters include the raspberry E4 promoter (U.S. Pat. Nos. 5,783,393 and 5,783,394), the 35S CaMV (Jones J D et al, 1992), the CsVMV promoter (Verdaguer B et al., 1998) and the melon actin promoter (published PCT application WO0056863). Exemplary tissue-specific promoters include the tomato E4 and E8 promoters (U.S. Pat. No. 5,859,330) and the tomato 2AII gene promoter (Van Haaren M J J et al., 1993).

In one preferred embodiment, HIO32.2 expression is under control of regulatory sequences from genes whose expression is associated with early seed and/or embryo development. Legume genes whose promoters are associated with early seed and embryo development include *V. faba* legumin (Baumlein et al., 1991, Mol Gen Genet. 225:121-8; Baumlein et al., 1992, Plant J 2:233-9), *V. faba* usp (Fiedler et al., 1993, Plant Mol Biol 22:669-79), pea convicilin (Bown et al., 1988, Biochem J 251:717-26), pea lectin (dePater et al., 1993, Plant Cell 5:877-86), *P. vulgaris* beta phaseolin (Bustos et al., 1991, EMBO J. 10: 1469-79), *P. vulgaris* DLEC2 and PHS [beta] (Bobb et al, 1997, Nucleic Acids Res 25:641-7), and soybean beta-Conglycinin, 7S storage protein (Chamberland et al., 1992, Plant Mol Biol 19:937-49). Cereal genes whose promoters are associated with early seed and embryo development include rice glutelin ("GluA-3," Yoshihara and Takaiwa, 1996, Plant Cell Physiol 37:107-11; "GluB-1," Takaiwa et al., 1996, Plant Mol Biol 30:1207-21; Washida et al., 1999, Plant Mol Biol 40:1-12; "Gt3," Leisy et al., 1990, Plant Mol Biol 14:41-50), rice prolamin (Zhou & Fan, 1993, Transgenic Res 2:141-6), wheat prolamin (Hammond-Kosack et al., 1993, EMBO J. 12:545-54), maize zein (Z4, Matzke et al., 1990, Plant Mol Biol 14:323-32), and barley *B-hordeins* (Entwistle et al., 1991, Plant Mol Biol 17:1217-31). Other genes whose promoters are associated with early seed and embryo development include oil palm GLO7A (7S globulin, Morcillo et al., 2001, Physiol Plant 112:233-243), *Brassica napus* napin, 2S storage protein, and napA gene (Josefsson et al., 1987, J Biol Chem 262:12196-201; Stalberg et al., 1993, Plant Mol Biol 1993 23:671-83; Ellerstrom et al., 1996, Plant Mol Biol 32:1019-27), *Brassica napus* oleosin (Keddie et al., 1994, Plant Mol Biol 24:327-40), *Arabidopsis* oleosin (Plant et al., 1994, Plant Mol Biol 25:193-205), *Arabidopsis* FAE1 (Rossak et al., 2001, Plant Mol Biol 46:717-25), *Canavalia gladiata* conA (Yamamoto et al., 1995, Plant Mol Biol 27:729-41), and *Catharanthus roseus* strictosidine synthase (Str, Ouwerkerk and Memelink, 1999, Mol Gen Genet. 261:635-43). In another preferred embodiment, regulatory sequences from genes expressed during oil biosynthesis are used (see, e.g., U.S. Pat. No. 5,952,544). Alternative promoters are from plant storage protein genes (Bevan et al, 1993, Philos Trans R Soc Lond B Biol Sci 342:209-15).

In yet another aspect, in some cases it may be desirable to inhibit the expression of endogenous HIO32.2 in a host cell. Exemplary methods for practicing this aspect of the invention include, but are not limited to antisense suppression (Smith, et al., 1988; van der Krol et al., 1988); co-suppression (Napoli, et al., 1990); ribozymes (PCT Publication WO 97/10328); and combinations of sense and antisense (Waterhouse, et al., 1998). Methods for the suppression of endogenous sequences in a host cell typically employ the transcription or transcription and translation of at least a portion of the sequence to be suppressed. Such sequences may be homologous to coding as well as non-coding regions of the endogenous sequence. Antisense inhibition may use the entire cDNA sequence (Sheehy et al., 1988), a partial cDNA sequence including fragments of 5' coding sequence, (Cannon et al., 1990), or 3' non-coding sequences (Ch'ng et al., 1989). Cosuppression techniques may use the entire cDNA sequence (Napoli et al., 1990; van der Krol et al., 1990), or a partial cDNA sequence (Smith et al., (1990).

Standard molecular and genetic tests may be performed to further analyze the association between a gene and an observed phenotype. Exemplary techniques are described below.

1. DNA/RNA Analysis

The stage- and tissue-specific gene expression patterns in mutant versus wild-type lines may be determined, for instance, by in situ hybridization. Analysis of the methylation status of the gene, especially flanking regulatory regions, may be performed. Other suitable techniques include overexpression, ectopic expression, expression in other plant species and gene knock-out (reverse genetics, targeted knock-out, viral induced gene silencing [VIGS, see Baulcombe D, 1999]).

In a preferred application expression profiling, generally by microarray analysis, is used to simultaneously measure differences or induced changes in the expression of many different genes. Techniques for microarray analysis are well known in the art (Schena M et al., Science (1995) 270:467-470; Baldwin D et al., 1999; Dangond F, Physiol Genomics (2000) 2:53-58; van Hal N L et al., J Biotechnol (2000) 78:271-280; Richmond T and Somerville S, Curr Opin Plant Biol (2000) 3:108-116). Expression profiling of individual tagged lines may be performed. Such analysis can identify other genes that are coordinately regulated as a consequence of the overexpression of the gene of interest, which may help to place an unknown gene in a particular pathway.

2. Gene Product Analysis

Analysis of gene products may include recombinant protein expression, antisera production, immunolocalization, biochemical assays for catalytic or other activity, analysis of phosphorylation status, and analysis of interaction with other proteins via yeast two-hybrid assays.

3. Pathway Analysis

Pathway analysis may include placing a gene or gene product within a particular biochemical, metabolic or signaling pathway based on its mis-expression phenotype or by sequence homology with related genes. Alternatively, analysis may comprise genetic crosses with wild-type lines and other mutant lines (creating double mutants) to order the gene in a pathway, or determining the effect of a mutation on expression of downstream "reporter" genes in a pathway.

Generation of Mutated Plants with an Altered Oil Content Phenotype

The invention further provides a method of identifying non-transgenic plants that have mutations in or an allele of endogenous HIO32.3 that confer a HIO32.3 phenotype to these plants and their progeny. In one method, called "TILLING" (for targeting induced local lesions in genomes), mutations are induced in the seed of a plant of interest, for example, using EMS treatment. The resulting plants are grown and self-fertilized, and the progeny are used to prepare DNA samples. HIO32.3-specific PCR is used to identify whether a mutated plant has a HIO32.3 mutation. Plants having HIO32.3 mutations may then be tested for altered oil content, or alternatively, plants may be tested for altered oil content, and then HIO32.3-specific PCR is used to determine whether a plant having altered oil content has a mutated HIO32.3 gene. TILLING can identify mutations that may alter the expression of specific genes or the activity of proteins encoded by these genes (see Colbert et al (2001) Plant Physiol 126:480-484; McCallum et al (2000) Nature Biotechnology 18:455-457).

In another method, a candidate gene Quantitative Trait Locus (QTLs) approach can be used in a marker-assisted breeding program to identify alleles of or mutations in the HIO32.3 gene or orthologs of HIO32.3 that may confer altered oil content (see Bert et al., Theor Appl Genet. 2003 June; 107(1):181-9; and Lionneton et al, Genome. 2002 December; 45(6):1203-15). Thus, in a further aspect of the invention, a HIO32.3 nucleic acid is used to identify whether a plant having altered oil content has a mutation in endogenous HIO32.3 or has a particular allele that causes altered oil content.

While the invention has been described with reference to specific methods and embodiments, it will be appreciated that various modifications and changes may be made without departing from the invention. All publications cited herein are expressly incorporated herein by reference for the purpose of describing and disclosing compositions and methodologies that might be used in connection with the invention. All cited patents, patent applications, and sequence information in referenced public databases are also incorporated by reference.

EXAMPLES

Example 1

Generation of Plants with a HIO32.2 Phenotype by Transformation with an Activation Tagging Construct Mutants were generated using the activation tagging "ACTTAG" vector, pSKI015 (GI#6537289; Weigel D et al., 2000). Standard methods were used for the generation of *Arabidopsis* transgenic plants, and were essentially as described in published application PCT WO183697. Briefly, T0 *Arabidopsis* (Col-0) plants were transformed with *Agrobacterium* carrying the pSKI015 vector, which comprises T-DNA derived from the *Agrobacterium* Ti plasmid, an herbicide resistance selectable marker gene, and the 4X CaMV 35S enhancer element. Transgenic plants were selected at the T1 generation based on herbicide resistance. T2 seed was collected from T1 plants and stored in an indexed collection, and a portion of the T2 seed was accessed for the screen.

Quantitative determination of seed fatty acid content was performed using the following methods. A sample of 15 to 20 T2 seeds from each line tested, which generally contained homozygous insertion, homozygous wild-type, and heterozygous genotypes in a standard 1:1:2 ratio, was massed on UMT-2 ultra-microbalance (Mettler-Toledo Co., Ohio, USA) and then transferred to a glass extraction vial. Lipids were extracted from the seeds and trans-esterified in 500 ul 2.5% $H_2SO_4$ in MeOH for 3 hours at 80° C., following the method of Browse et al. (Biochem J 235:25-31, 1986) with modifications. A known amount of heptadecanoic acid was included in the reaction as an internal standard. 750 ul of water and 400 ul of hexane were added to each vial, which was then shaken vigorously and allowed to phase separate. Reaction vials were loaded directly onto GC for analysis and the upper hexane phase was sampled by the autosampler. Gas chromatography with Flame Ionization detection was used to separate and quantify the fatty acid methyl esters. Agilent 6890 Plus GC's were used for separation with Agilent Innowax columns (30 m×0.25 mm ID, 250 um film thickness). The carrier gas was Hydrogen at a constant flow of 2.5 ml/minute. 1 ul of sample was injected in splitless mode (inlet temperature 220° C., Purge flow 15 ml/min at 1 minute). The oven was programmed for an initial temperature of 105° C., initial time 0.5 minutes, followed by a ramp of 60° C. per minute to 175° C., a 40° C./minute ramp to 260° C. with a final hold time of 2 minutes. Detection was by Flame Ionization (Temperature 275° C., Fuel flow 30.0 ml/min, Oxidizer 400.0 ml/min). Instrument control and data collection and analysis were monitored using the Millennium Chromatography Management System (Version 3.2, Waters Corporation, Milford, Mass.). Integration and quantification were performed automatically, but all analyses were subsequently examined manually to verify correct peak identification and acceptable signal to noise ratio before inclusion of the derived results in the study.

The ACTTAG line designated WO00082263 was identified as having a high oil phenotype. Specifically, oil constituted 36.3% of seed mass (w/w) compared to an average oil content of 27.0% of other ACTTAG lines grown and analyzed in the same conditions (e.g., reference lines). Reanalysis of the same seed was performed in duplicate. This analysis confirmed an increase in oil content relative to controls. It was concluded that the presence of the ACTTAG locus can increase seed oil content between 7% and 11% relative to controls. It is determined that the high oil phenotype is dominant based on oil content of seeds from genotyped individuals.

Example 2

Characterization of the T-DNA Insertion in Plants Exhibiting the Altered Oil Content Phenotype We performed standard molecular analyses, essentially as described in patent application PCT WO0183697, to determine the site of the T-DNA insertion associated with the altered oil content phenotype. Briefly, genomic DNA was extracted from plants exhibiting the altered oil content phenotype. PCR, using primers specific to the pSKI015 vector, confirmed the presence of the 35S enhancer in plants from line W000082263, and Southern blot analysis verified the genomic integration of the ACTTAG T-DNA and showed the presence of a single T-DNA insertion in the transgenic line.

Plasmid rescue was used to recover genomic DNA flanking the T-DNA insertion, which was then subjected to sequence analysis using a basic BLASTN search and/or a search of the Arabidopsis Information Resource (TAIR) database (publicly available at the Arabidopsis Information Resource website). There was sequence identity to BAC clone T23J7 (GI#4741184), chromosome 3. Sequences from nucleotides 16030-16423 and 16443-17200 were recovered, placing the left border junction upstream of nucleotide 16423 (GI#4741184) and downstream of nucleotide 15443. The sequences from nucleotides 15424-16442 of BAC clone T23J7, chromosome 3 (GI#4741184) are deleted in the mutant chromosome.

To determine whether the T-DNA insertion causes the high seed oil phenotype co-segregation of the high seed oil phenotype and the presence of the T-DNA was tested. Eighteen T2 plants were grown to maturity and seed harvested from these plants was used to determine the seed oil phenotype. The seed oil content from these was determined as described in Example 1. The genotype of the T2 seed was inferred by analyzing the T3 seed for the presence or absence of the T-DNA at the site of the insertion by PCR using primers that are specific to the corresponding genomic region and the T-DNA. The results show that the average oil content of T3 seed containing the T-DNA insert was higher than those families lacking the insert. T2 individuals homozygous for the T-DNA at this locus produced seed with an oil content of 107.5% compared to progeny lacking the T-DNA. T2 individuals hemizygous for these loci produced seed with an oil content of 112.7% compared to progeny lacking the T-DNA. Because the homozygotes and hemizygotes for the high oil loci display a similar increase in oil content, we conclude that the T-DNA is linked with the high oil phenotype and the phenotype is caused by a dominant mutation.

Sequence analysis revealed that the left border of the T-DNA insert was about 954 base pairs 3' of the translation start site of the gene whose nucleotide sequence is presented as SEQ ID NO: 1 which we designated HIO32.2.

Example 3

Analysis of Arabidopsis HIO32.2 Sequence

Sequence analyses were performed with BLAST (Altschul et al., 1997, J. Mol. Biol. 215:403-410), PFAM (Bateman et al., 1999, Nucleic Acids Res 27:260-262), PSORT (Nakai K, and Horton P, 1999, Trends Biochem Sci 24:34-6), and/or CLUSTAL (Thompson J D et al, 1994, Nucleic Acids Res 22:4673-4680).

The TAIR prediction of At3g47710 corresponds to amino acid residues 15-92 of Genbank prediction (gi|22331644). In neither cases is the residue immediately follows the translation initiation codon (ATG) a guanosine (G), which is typical for most genes in Arabidopsis. It is likely that the predicted gene structure for At3g47710 has an atypical residue (thymidine, T) following the translation initiation codon (ATG). This proposal is supported by the fact that three Arabidopsis homologues of At3g47710 (At1g74500, At5g39860 and gi|21617952) whose gene structures are supported by cDNAs have the sequence ATGT at the initiation codons.

BLASTN Against ESTs:

No Arabidopsis EST shows exact match to the candidate gene At3g47710. However, ESTs corresponding to Arabidopsis homologues of At3g47710 can be identified. These genes are described in the BLASTP analysis below.

There are also other similar plant ESTs showing similarity to At3g47700. If possible, ESTs contigs of each species were made. The best hit for each of the following species are listed below and included in the "Orthologue Table" below: *Glycine max, Lycopersicon esculentun, Gossypium arboreum, Zea mays, Oryza sativa, Triticum aestivum, Solanum tuberosum*.

1. One EST contig from soybean (*Glycine max*)
>gi|16344264|gb|BI969859.1|BI969859 GM830009A23D05
>gi|16344265|gb|BI969860.1|BI969860 GM830009A23D06
>gi|10848131|gb|BF070679.1|BF070679 st23h10.y1
>gi|19345905|gb|BM890785.1|BM890785 sam07g12.y1
>gi|7925404|gb|AW831369.1|AW831369 sm24d03.y1
Score=310 (114.2 bits), Expect=2.8e-33

These ESTs were isolated from mixed tissues of various developmental stages or from germinating shoots.

The contigged sequence is presented as SEQ ID NO:3 below.

2. One EST from wheat (*Triticum aestivum*)
>gi|201034721|dbj|BJ282051.1|BJ282051 BJ282051 from an unpublished cDNA library.
Score=286 (105.7 bits), Expect=9.9e-31

The EST described above (gi|20103472) encompasses the following EST
>gi|20106345|dbj|BJ287183.1|BJ287183 BJ287183 from an unpublished cDNA library.

3. One EST from tomato (*Lycopersicon esculentum*)
>gi|7409117|gb|AW647879.1|AW647879 EST326333 tomato germinating seedlings, TAMU library
Score=278 (102.9 bits), Expect=6.9e-30

4. One EST from potato (*Solanum tuberosum*)
>gi|21375581|gb|BQ516712.1|BQ516712 EST624127 from a library constructed with mixed tomato tissues
Score=265 (98.3 bits), Expect=1.7e-28

The EST described above (gi|20103472) encompasses the following EST
>gi|21375582|gb|BQ516713.1|BQ516713 EST624128 from a library constructed with mixed tomato tissues 5. One EST from rice (*Oryza sativa*)
>gi|8334893|gb|BE039877.1|BE039877 OC09D12 OC Oryza sativa cDNA 5', mRNA from 1 week old roots
Score=228 (85.3 bits), Expect=1.4e-24

6. One EST from maize (*Zea mays*)
>gi|18173123|gb|BM348511.1|BM348511 MEST292-A06.T3 ISUM5-RNA Zea mays cDNA clone isolated from a B73 Maize library constructed with tissues from various stages and treated with a variety of hormones
Score=202 (76.2 bits), Expect=7.9e-22, 7. One EST from tree cotton (*Gossypium arboreum*)
>gi|18098731|gb|BM357985.1|BM357985 GA_Ea0003E23r Gossypium arboreum 7-10 dpa fiber library
Score=197 (74.4 bits), Expect=2.7e-21

BLASTP against all.aa results:
At3g47710 has homology to a small number of plant proteins. The top 7 BLAST hits are listed below and are included in the "Orthologue Table" below.

1. Itself (3 redundant entries)
>gi|22331645|ref|NP_190355.2| bHLH protein; protein id: At3g47710.1 *[Arabidopsis thaliana]*
Score=123 bits (309), Expect=5e-28

The following 2 sequences are redundant entries of At3g47710 based on Genbank annotation. The predicted gene structure for At3g47710 from gi|7487374 and gi|4741188 corresponds to amino acid residues 15-92 of gi|22331645.

>gi|7487374|pir||T07710 hypothetical protein T23J7.40—*Arabidopsis thaliana*
>gi|4741188|emb|CAB41854.1| hypothetical protein [*Arabidopsis thaliana*]
Score=111 bits (277), Expect=2e-24

2. At1g74500 from *Arabidopsis* (4 redundant entries)
>gi|15221264|ref|NP_177590.1| bHLH protein; protein id: At1g74500.1, supported by cDNA: 519. [*Arabidopsis thaliana*]
>gi|25406349|pir||A96774 probable DNA-binding protein F1M20.18 [imported]—*Arabidopsis thaliana*
>gi|12324788|gb|AAG52350.1|AC01765_2 putative DNA-binding protein; 54988-54618 [*Arabidopsis thaliana*]
>gi|21593858|gb|AAM65825.1| putative DNA-binding protein [*Arabidopsis thaliana*]
Score=78.2 bits (191), Expect=2e-14

3. A DNA-binding protein-like protein from chromosome 3 of *Arabidopsis* (2 redundant entries in Genbank)
>gi|21617952|gb|AAM67002.1| DNA-binding protein-like [*Arabidopsis thaliana*]
Score=73.9 bits (180), Expect=4e-13

This is a gene represented by a cDNA that is mapped to chromosome 3 of *Arabidopsis*. There is no TAIR annotation of this gene.

The following entry is likely to be a redundant entry of gi|21617952, because BLASTN shows that the sequences gi|21617952 and gi|9294226 are localized to the same place in the *Arabidopsis* genome. The sequences gi|21617952 and gi|9294226 differ by a few amino acids. These are likely to be sequencing errors or single nucleotide polymorphisms with little or no effect on activity.

>gi|9294226|dbj|BAB02128.1| DNA-binding protein-like [*Arabidopsis thaliana*]
Score=74.7 bits (182), Expect=2e-13

4. At5g39860 of *Arabidopsis* (3 redundant entries in Genbank)
>gi|15242499|ref|NP_198802.1| bHLH protein; protein id: At5g39860.1 [*Arabidopsis thaliana*]
>gi|10176978|dbj|BAB10210.1| DNA-binding protein-like [*Arabidopsis thaliana*]
>gi|21593819|gb|AAM65786.1| DNA-binding protein-like [*Arabidopsis thaliana*]
Score=70.9 bits (172), Expect=4e-12

5. At5g15160 of *Arabidopsis* (3 redundant entries in Genbank)
>gi|15242227|ref|NP_197020.1| bHLH protein; protein id: At5g1560.1 [*Arabidopsis thaliana*]
>gi|11357892|pir||T49951 hypothetical protein F8M21.50—*Arabidopsis thaliana*
>gi|7671485|emb|CAB89326.1| putative protein [*Arabidopsis thaliana*]
Score=69.7 bits (169), Expect=8e-12

6. A hypothetical protein from rice (*Oryza sativa*)
>gi|21671920|gb|AAM74282.1|AC083943_22 Hypothetical protein similar to putative DNA binding proteins [*Oryza sativa* (japonica cultivar-group)]
Score=54.3 bits (129), Expect=4e-07

7. A putative protein from rice (*Oryza sativa*)
>gi|10241623|emb|CAC09463.1| putative DNA binding protein [*Oryza sativa* (indica cultivar-group)]
Score=53.5 bits (127), Expect=6e-07

| Ortholog Gene Name | Species | GI # | % ID to HIO32.2 | Score(s) (BLAST, Clustal, etc.) | Coordinates of protein motif(s) | % ID to NEWGENE motif or to Pfam/other consensus |
|---|---|---|---|---|---|---|
| A hypothetical protein from rice | *Oryza saliva (japonica* cultivar-group) | >gi|21671920 | Length = 88 Identities = 44/93 (47%), Positives = 65/93 (69%) | BLASTP Score = 54.3 bits (129), Expect = 4e−07 | SM00353: aa 4-56 PF00010: aa 5-61 | SM00353: Score = −0.5, E value = 0.13 PF00010: Score = 11.4, E value = 0.0018 |
| A putative protein from rice | *Oryza sativa (indica* cultivar-group) | >gi|10241623 | Length = 104 Identities = 53/102 (51%), Positives = 70/102 (68%) | BLASTP Score = 53.5 bits (127), Expect = 6e−07 | SM00353: aa 26-77 PF00010: aa 23-72 | SM00353: Score = 13.7, E value = 0.0097 PF00010: Score = 7.9, E value = 0.017 |
| An EST contig from soybean | *Glycine max* | >gi|16344264 >gi|16344265 >gi|10848131 >gi|19345905 >gi|7925404 | Partial sequence, using reading frame + 1 Length = 99 Identities = 66/93 (70%), Positives = 83/93 (89%) | BLASTN Score = 310 (114.2 bits), Expect = 2.8e−33, P = 2.8e−33 | SM00353: aa 18-73 PF00010: aa 18-68 | SM00353: Score = 16.2, E value = 0.0049 PF00010: Score = 11.0, E value = 0.0076 |
| A wheat EST | *Triticum aestivum* | >gi|20103472 | Partial sequence, using reading frame + 3 Length = 116 Identities = 64/93 (68%), Positives = 79/93 (84%) | BLASTN Score = 286 (105.7 bits), Expect = 9.9e−31, P = 9.9e−31 | SM00353: aa 41-90 PF00010: aa 29-85 | SM00353: Score = 11.1, E value = 0.019 PF00010: Score = 0.4, E value = 0.11 |
| A tomato EST | *Triticum aestivum* | >gi|7409117 | Partial sequence, using reading frame + 2 Length = 91 Identities = 65/93 (69%), Positives = 77/93 (82%) | BLASTN Score = 278 (102.9 bits), Expect = 6.9e−30, P = 6.9e−30 | SM00353: aa 10-64 PF00010: aa 9-59 | SM00353: Score = 12.6, E value = 0.013 PF00010: Score = 6.9, E value = 0.021 |
| A potato EST | *Solanum tuberosum* | >gi|21375581 | Partial sequence, using reading frame + 1 Length = 109 Identities = 61/95 (64%), Positives = 77/95 (81%) | BLASTN Score = 265 (98.3 bits), Expect = 1.7e−28, P = 1.7e−28 | SM00353: aa 16-71 PF00010: aa 13-66 | SM00353: Score = 9.1, E value = 0.033 PF00010: Score = 1.9, E value = 0.074 |

-continued

| Ortholog Gene Name | Species | GI # | % ID to HIO32.2 | Score(s) (BLAST, Clustal, etc.) | Coordinates of protein motif(s) | % ID to NEWGENE motif or to Pfam/other consensus |
|---|---|---|---|---|---|---|
| A rice EST from root | Oryza sativa | >gi\|8334893 | Partial sequence, using reading frame + 2 Length = 76 Identities = 52/77 (67%), Positives = 64/77 (83%) | BLASTN Score = 228 (85.3 bits), Expect = 1.4e-24, P = 1.4e-24 | SM00353: aa 2-49 PF00010: aa 1-44 | SM00353: Score = 7.9, E value = 0.043 PF00010: Score = -1.0, E value = 0.14 |
| A maize EST | Zea mays | >gi\|18173123 | Partial sequence, using reading frame - 2 Length = 121 Identities = 54/104 (51%), Positives = 74/104 (71%) | BLASTN Score = 202 (76.2 bits), Expect = 7.9e-22, P = 7.9e-22 | SM00353: aa 42-94 PF00010: aa 37-89 | SM00353: Score = 12.7, E value = 0.013 PF00010: Score = 5.2, E value = 0.032 |
| A cotton fiber EST | Gossypium arboreum | >gi\|18098731 | Partial sequence, using reading frame - 2 Length = 85 Identities = 41/83 (49%), Positives = 62/83 (74%) | BLASTN Score = 197 (74.4 bits), Expect = 2.7e-21, P = 2.7e-21 | SM00353: aa 7-58 PF00010: aa 4-53 | SM00353: Score = 26.3, E value = 7.6e-05 PF00010: Score = 14.4, E value = 0.0033 |
| Closest *Arabidopsis* homologs: | | | | | | |
| At1g74500 | Arabidopsis thaliana | >gi\|15221264 >gi\|25406349 >gi\|12324788 >gi\|21593858 | Length = 93 Identities = 58/93 (62%), Positives = 77/93 (82%) | BLASTP Score = 78.2 bits (191), Expect = 2e-14 | SM00353: aa 16-67 PF00010: aa 7-62 | SM00353: Score = 21.7, E value = 0.0011 PF00010: Score = -14.3, E value = 0.033 |
| A DNA-binding protein-like protein | Arabidopsis thaliana | >gi\|21617952 | Length = 92 Identities = 57/93 (61%), Positives = 74/93 (79%) | BLASTP Score = 73.9 bits (180), Expect = 4e-13 | SM00353: aa 10-65 PF00010: aa 6-60 | SM00353: Score = 7.8, E value = 0.048 PF00010: Score = -0.9, E value = 0.15 |
| At5g39860 | Arabidopsis thaliana | >gi\|15242499 >gi\|10176978 >gi\|21593819 | Length = 92 Identities = 55/93 (59%), Positives = 71/93 (76%) | BLASTP Score = 70.9 bits (172), Expect = 4e-12 | SM00353: aa 10-65 PF00010: aa 5-60 | SM00353: Score = 3.6, E value = 0.15 PF00010: Score = -0.3, E value = 0.13 |
| At5g15160 | Arabidopsis thaliana | >gi\|15242227 >gi\|11357892 >gi\|7671485 | Length = 94 Identities = 53/91 (58%), Positives = 71/91 (78%) | BLASTP Score = 69.7 bits (169), Expect = 8e-12 | SM00353: aa 6-61 PF00010: aa 11-66 | SM00353: Score = 4.8, E value = 0.036 PF00010: Score = -9.6, E value = 0.029 |

At3g47710 is a non-secretory protein that lacks transmembrane domain (predicted by TMHMM) and signal peptide (predicted by SignalP). PSORT2 predicts At3g47710 to be localized to the mitochondria (64% mitochondrial, 24% nuclear, 8% cytoplasmic, 4% peroxisomal). However, Predator analysis gives contradictory results and suggests that At3g47710 is localized to neither the mitochondria nor the plastid (5% mitochondrial, 0% plastid). Therefore, Pfam analysis showed that At3g47710 shows weak homology to the helix-loop-helix DNA-binding domain (PF00010, SM00353). The basic helix-loop-helix proteins (bHLH) are a group of eukaryotic transcription factors that have diverse functions. These transcription factors are characterized by a highly conserved bHLH domain that mediates DNA binding and dimerisation with other proteins (Littlewood and Evan, 1995 Protein Profile 2,621-702).

A number of *Arabidopsis* bHLH proteins have been characterized and shown to be important for diverse functions such as development of carpel margin, fruit dehiscence, light signal transduction, root hair development and trichome development (Heisler et al., 2001 Development. 128, 1089-1098; Rajani and Sundaresan, 2001, Curr Biol. 11, 1914-1922; Huq and Quail, 2002 EMBO J. 21, 2441-2450; Wada et al., 2002, Development. 129, 5409-5419; Smolen et al., 2002, Genetics. 161, 1235-1246; Sawa, 2002, DNA Res. 9, 31-34). It should be noted that BLASTP analysis of At3g47710 did not identify functionally characterized bHLH proteins in *Arabidopsis*, suggesting that At3g47710 is a distant family member to these bHLH proteins. Nonetheless, it is conceivable that over-expression of the transcription factor At3g47710 may increase seed oil content by altering expression of downstream genes in either the nucleus or the mitochondria.

| Model | Domain | seq-f | seq-t | hmm-f | hmm-t | | score | E-value |
|---|---|---|---|---|---|---|---|---|
| SM00353 | 1/1 | 16 | 66 | ... 1 | 61 | [ ] | 9.8 | 0.028 |
| PF00010 | 1/1 | 16 | 61 | ... 1 | 53 | [ ] | 1.9 | 0.073 |

Example 4

Confirmation of Phenotype/Genotype Association

RT-PCR analysis showed that the HIO32.2 gene was overexpressed in plants from the line displaying the HIO32.2 phenotype. Specifically, RNA was extracted from rosette leaves and/or siliques of plants exhibiting the HIO32.2 phenotype collected at a variety of developmental stages and pooled. RT-PCR was performed using primers specific to the sequence presented as SEQ ID NO:1, to other predicted genes in the vicinity of the T-DNA insertion, and to a constitutively expressed actin gene (positive control). The results showed that in plants displaying the HIO32.2 phenotype, mRNA for the HIO32.2 gene is up-regulated in leaves and down-regulated in siliques.

The dominant inheritance pattern of the HIO32.2 phenotype is confirmed through genetic analysis. In general, genetic analysis involves the production and analysis of F1 hybrids. Typically, F1 crosses are carried out by collecting pollen from T2 plants, which is used to pollinate wild type plants. Such crosses are carried out by taking about 4 flowers from each selected individual plants, and using the T2 flower as the male pollen donor and flowers of the wild type plants as the female. 4-5 crosses are done for an individual of interest. Seed formed from crosses of the same individual are pooled, planted and grown to maturity as F1 hybrids.

Example 5

Recapitulation of the High Oil Phenotype

To confirm whether over-expression of At3g47710 causes a high seed oil phenotype, oil content in seeds from transgenic plants over-expressing this gene was compared with oil content in seeds from non-transgenic control plants. To do this, At3g47710 was cloned into a plant transformation vector behind the strong constitutive CsVMV promoter and transformed into *Arabidopsis* plants using the floral dip method. The plant transformation vector contains the nptII gene, which provides resistance to kanamycin, and serves as a selectable marker. Seed from the transformed plants were plated on agar medium containing kanamycin. After 7 days, transgenic plants were identified as healthy green plants and transplanted to soil. Non-transgenic control plants were germinated on agar medium, allowed to grow for 7 days and then transplanted to soil. Twenty-two transgenic seedlings and 10 non-transgenic control plants were transplanted to random positions in the same 32 cell flat. The plants were grown to maturity, allowed to self-fertilize and set seed. Seed was harvested from each plant and its oil content estimated by Near Infrared (NIR) Spectroscopy using methods described below.

NIR infrared spectra were captured using a Bruker 22 N/F near infrared spectrometer. Bruker Software was used to estimate total seed oil and total seed protein content using NIR data from the samples and reference methods according to the manufacturer's instructions. An oil content predicting calibration was developed following the general method of AOCS Procedure Am1-92, Official Methods and Recommended Practices of the American Oil Chemists Society, 5th Ed., AOCS, Champaign Ill.). The calibration allowing NIR predictions of Crude Oil Crude Oil ASE (Ren Oil, Accelerated Solvent Extraction) was developed.

The effect of over-expression of At3g47710 on seed oil has been tested in five experiments. In four experiments, the plants over-expressing At3g47710 had higher seed oil content than the control plants grown in the same flat. Across the experiments, the average seed oil content of plants over-expressing At3g47710 was 3.5% greater than the untransformed controls. The in seed oil content in plants over-expressing At3g47710 was significantly greater than non-transgenic control plants (two-way ANOVA; P=0.0066), see Table 1.

TABLE 1

| Experiment | Plant ID | Transgene | Predicted average | Relative value average |
|---|---|---|---|---|
| 1 | DX02948001 | CsVMV::HIO32.2 | 31.2429 | 93.4123 |
| 1 | DX02948003 | CsVMV::HIO32.2 | 34.8987 | 104.3425 |
| 1 | DX02948004 | CsVMV::HIO32.2 | 32.9915 | 98.6401 |
| 1 | DX02948005 | CsVMV::HIO32.2 | 35.0001 | 104.6456 |
| 1 | DX02948006 | CsVMV::HIO32.2 | 36.5424 | 109.2568 |
| 1 | DX02948007 | CsVMV::HIO32.2 | 36.7931 | 110.0065 |
| 1 | DX02948008 | CsVMV::HIO32.2 | 36.4274 | 108.9132 |
| 1 | DX02948009 | CsVMV::HIO32.2 | 35.0468 | 104.7852 |
| 1 | DX02948011 | CsVMV::HIO32.2 | 34.2905 | 102.5239 |
| 1 | DX02948013 | CsVMV::HIO32.2 | 33.4158 | 99.9088 |
| 1 | DX02948014 | CsVMV::HIO32.2 | 34.1728 | 102.1721 |
| 1 | DX02948015 | CsVMV::HIO32.2 | 31.6579 | 94.6528 |
| 1 | DX02947001 | None | 35.6386 | 106.5548 |
| 1 | DX02947002 | None | 34.0045 | 101.6688 |
| 1 | DX02947003 | None | 32.578 | 97.4039 |
| 1 | DX02947004 | None | 33.5877 | 100.4227 |
| 1 | DX02947005 | None | 33.0303 | 98.7563 |
| 1 | DX02947006 | None | 34.3919 | 102.8273 |
| 1 | DX02947007 | None | 33.1974 | 99.2558 |
| 1 | DX02947008 | None | 31.142 | 93.1104 |
| 2 | Z003900001 | CsVMV::HIO32.2 | 33.6896 | 106.2791 |
| 2 | Z003900002 | CsVMV::HIO32.2 | 33.3141 | 105.0947 |
| 2 | Z003900003 | CsVMV::HIO32.2 | 35.6526 | 112.4718 |
| 2 | Z003900004 | CsVMV::HIO32.2 | 27.8247 | 87.7776 |
| 2 | Z003900005 | CsVMV::HIO32.2 | 33.1646 | 104.6231 |
| 2 | Z003900006 | CsVMV::HIO32.2 | 37.0337 | 116.8286 |
| 2 | Z003900008 | CsVMV::HIO32.2 | 34.6903 | 109.4361 |
| 2 | Z003900009 | CsVMV::HIO32.2 | 30.981 | 97.7346 |
| 2 | Z003900010 | CsVMV::HIO32.2 | 39.056 | 123.2082 |
| 2 | Z003900011 | CsVMV::HIO32.2 | 37.1317 | 117.1378 |
| 2 | Z003900013 | CsVMV::HIO32.2 | 32.409 | 102.2392 |
| 2 | Z003900014 | CsVMV::HIO32.2 | 36.3444 | 114.6543 |
| 2 | Z003900015 | CsVMV::HIO32.2 | 36.8128 | 116.1318 |
| 2 | Z003900017 | CsVMV::HIO32.2 | 38.4427 | 121.2736 |
| 2 | Z003900018 | CsVMV::HIO32.2 | 33.6492 | 106.1516 |
| 2 | Z003900020 | CsVMV::HIO32.2 | 30.8397 | 97.2888 |
| 2 | Z003900021 | CsVMV::HIO32.2 | 35.9108 | 113.2864 |
| 2 | Z003890001 | None | 36.4237 | 114.9044 |
| 2 | Z003890003 | None | 32.4789 | 102.4599 |
| 2 | Z003890004 | None | 33.9902 | 107.2273 |
| 2 | Z003890005 | None | 29.5647 | 93.2666 |
| 2 | Z003890006 | None | 31.4827 | 99.3173 |
| 2 | Z003890007 | None | 27.8273 | 87.7857 |
| 2 | Z003890008 | None | 26.2013 | 82.6561 |
| 2 | Z003890009 | None | 34.3203 | 108.269 |
| 2 | Z003890010 | None | 33.0031 | 104.1136 |
| 3 | Z003978002 | CsVMV::HIO32.2 | 33.4407 | 97.8939 |
| 3 | Z003978003 | CsVMV::HIO32.2 | 36.4683 | 106.7568 |
| 3 | Z003978004 | CsVMV::HIO32.2 | 34.9617 | 102.3464 |
| 3 | Z003978005 | CsVMV::HIO32.2 | 34.7488 | 101.7233 |
| 3 | Z003978007 | CsVMV::HIO32.2 | 31.0467 | 90.8856 |
| 3 | Z003978008 | CsVMV::HIO32.2 | 36.6832 | 107.3859 |
| 3 | Z003978010 | CsVMV::HIO32.2 | 34.8046 | 101.8866 |
| 3 | Z003978011 | CsVMV::HIO32.2 | 26.9809 | 78.9835 |
| 3 | Z003978012 | CsVMV::HIO32.2 | 32.4106 | 94.8785 |
| 3 | Z003978014 | CsVMV::HIO32.2 | 35.5825 | 104.1638 |
| 3 | Z003978015 | CsVMV::HIO32.2 | 33.9295 | 99.3247 |
| 3 | Z003978016 | CsVMV::HIO32.2 | 34.9754 | 102.3866 |
| 3 | Z003978017 | CsVMV::HIO32.2 | 33.5072 | 98.0887 |
| 3 | Z003978018 | CsVMV::HIO32.2 | 35.3474 | 103.4756 |
| 3 | Z003978019 | CsVMV::HIO32.2 | 33.4171 | 97.8248 |
| 3 | Z003978022 | CsVMV::HIO32.2 | 31.2548 | 91.4948 |
| 3 | Z003994001 | None | 35.8594 | 104.9744 |
| 3 | Z003994002 | None | 34.3685 | 100.61 |
| 3 | Z003994003 | None | 34.7967 | 101.8634 |
| 3 | Z003994004 | None | 36.266 | 106.1646 |
| 3 | Z003994005 | None | 30.8633 | 90.3488 |
| 3 | Z003994006 | None | 32.8165 | 96.0666 |
| 3 | Z003994007 | None | 36.5016 | 106.8543 |
| 3 | Z003994008 | None | 34.9869 | 102.4202 |
| 3 | Z003994009 | None | 30.7767 | 90.0952 |

TABLE 1-continued

| Experiment | Plant ID | Transgene | Predicted average | Relative value average |
|---|---|---|---|---|
| 3 | Z003994010 | None | 34.3659 | 100.6024 |
| 4 | DX06941001 | CsVMV::HIO32.2 | 33.9232 | 104.5537 |
| 4 | DX06941002 | CsVMV::HIO32.2 | 33.6401 | 103.6812 |
| 4 | DX06941003 | CsVMV::HIO32.2 | 35.7409 | 110.1562 |
| 4 | DX06941004 | CsVMV::HIO32.2 | 31.9439 | 98.4536 |
| 4 | DX06941005 | CsVMV::HIO32.2 | 31.3507 | 96.6252 |
| 4 | DX06941006 | CsVMV::HIO32.2 | 32.5406 | 100.2926 |
| 4 | DX06941007 | CsVMV::HIO32.2 | 33.1874 | 102.286 |
| 4 | DX06941008 | CsVMV::HIO32.2 | 34.0966 | 105.0881 |
| 4 | DX06941009 | CsVMV::HIO32.2 | 34.7597 | 107.132 |
| 4 | DX06941010 | CsVMV::HIO32.2 | 32.8897 | 101.3686 |
| 4 | DX06941011 | CsVMV::HIO32.2 | 34.0769 | 105.0275 |
| 4 | DX06941012 | CsVMV::HIO32.2 | 32.9075 | 101.4232 |
| 4 | DX06941013 | CsVMV::HIO32.2 | 36.1765 | 111.4985 |
| 4 | DX06941014 | CsVMV::HIO32.2 | 34.3151 | 105.7617 |
| 4 | DX06941015 | CsVMV::HIO32.2 | 31.8685 | 98.2211 |
| 4 | DX06941016 | CsVMV::HIO32.2 | 32.2279 | 99.3287 |
| 4 | DX06941017 | CsVMV::HIO32.2 | 35.2172 | 108.542 |
| 4 | DX06941018 | CsVMV::HIO32.2 | 30.4763 | 93.9302 |
| 4 | DX06941019 | CsVMV::HIO32.2 | 30.573 | 94.2281 |
| 4 | DX06941020 | CsVMV::HIO32.2 | 32.4645 | 100.0581 |
| 4 | DX06941021 | CsVMV::HIO32.2 | 36.0598 | 111.139 |
| 4 | DX06941022 | CsVMV::HIO32.2 | 31.4834 | 97.0342 |
| 4 | DX06959001 | None | 32.2856 | 99.5067 |
| 4 | DX06959002 | None | 31.1875 | 96.122 |
| 4 | DX06959003 | None | 34.4381 | 106.1409 |
| 4 | DX06959004 | None | 32.1773 | 99.1728 |
| 4 | DX06959005 | None | 33.4702 | 103.1577 |
| 4 | DX06959006 | None | 33.1607 | 102.2038 |
| 4 | DX06959007 | None | 33.1406 | 102.1416 |
| 4 | DX06959008 | None | 29.7743 | 91.7666 |
| 4 | DX06959009 | None | 32.3769 | 99.7879 |
| 4 | DX06959010 | None | 32.3769 | 99.7879 |
| 5 | DX06942001 | CsVMV::HIO32.2 | 32.4339 | 104.7283 |
| 5 | DX06942002 | CsVMV::HIO32.2 | 32.5468 | 105.0928 |
| 5 | DX06942003 | CsVMV::HIO32.2 | 31.6804 | 102.2953 |
| 5 | DX06942004 | CsVMV::HIO32.2 | 31.2728 | 100.9792 |
| 5 | DX06942005 | CsVMV::HIO32.2 | 34.0027 | 109.7938 |
| 5 | DX06942006 | CsVMV::HIO32.2 | 31.9079 | 103.0297 |
| 5 | DX06942007 | CsVMV::HIO32.2 | 31.0441 | 100.2405 |
| 5 | DX06942008 | CsVMV::HIO32.2 | 30.5782 | 98.7361 |
| 5 | DX06942009 | CsVMV::HIO32.2 | 35.4122 | 114.3452 |
| 5 | DX06942010 | CsVMV::HIO32.2 | 32.6468 | 105.4156 |
| 5 | DX06942011 | CsVMV::HIO32.2 | 35.5334 | 114.7364 |
| 5 | DX06942012 | CsVMV::HIO32.2 | 31.0164 | 100.1512 |
| 5 | DX06942014 | CsVMV::HIO32.2 | 29.8991 | 96.5435 |
| 5 | DX06942015 | CsVMV::HIO32.2 | 33.7667 | 109.0383 |
| 5 | DX06942016 | CsVMV::HIO32.2 | 31.959 | 103.1948 |
| 5 | DX06942017 | CsVMV::HIO32.2 | 32.7295 | 105.6828 |
| 5 | DX06942018 | CsVMV::HIO32.2 | 32.3263 | 104.3809 |
| 5 | DX06942019 | CsVMV::HIO32.2 | 33.0989 | 106.8755 |
| 5 | DX06942020 | CsVMV::HIO32.2 | 29.9662 | 96.7602 |
| 5 | DX06960001 | None | 28.8877 | 93.2776 |
| 5 | DX06960002 | None | 33.7045 | 108.8311 |
| 5 | DX06960003 | None | 29.816 | 96.275 |
| 5 | DX06960004 | None | 32.7046 | 105.6022 |
| 5 | DX06960005 | None | 31.3342 | 101.1775 |
| 5 | DX06960006 | None | 31.0325 | 100.2031 |
| 5 | DX06960007 | None | 32.8594 | 106.1021 |
| 5 | DX06960008 | None | 28.4125 | 91.7432 |
| 5 | DX06960009 | None | 30.4112 | 98.1969 |
| 5 | DX06960010 | None | 30.5333 | 98.5913 |

REFERENCES

Altschul, S. F. et al., *J. Mol. Biol.* 215:403-410, 1990.
Altschul, S. F. et al., *Nucleic Acids Res.* 25:3389-3402, 1997.
Ausubel F M et al. Current Protocols in Molecular Biology, John Wiley & Sons, New York, N.Y., 1993.
Baldwin D et al., *Cur Opin Plant Biol.* 2(2):96-103, 1999.
Bateman et al., 1999, Nucleic Acids Res 27:260-262.
Baulcombe D, *Arch Virol Suppl* 15:189-201, 1999.
Cannon et al., Plant Molec. Biol. (1990) 15:39-47.
Ch'ng et al., Proc. Natl. Acad. Sci. USA (1989) 86:10006-10010
Christensen S et al., 9th International Conference on *Arabidopsis* Research. Univ. of Wisconsin-Madison, Jun. 24-28, 1998. Abstract 165.
Christou et al., Proc. Natl. Acad. Sci. USA (1989) 86:7500-7504.
Cough, S J and Bent, A F, *the Plant Journal* 16(6): 735-743, 1998.
De Block et al., Plant Physiol. (1989) 91:694-701.
Dieffenbach C and Dveksler G (Eds.) PCR Primer: A Laboratory Manual, Cold Spring Harbor Laboratory Press, NY, 1989.
Everett et al., Bio/Technology (1987) 5:1201
Feldmann et al., *Science* 243: 1351-1354, 1989.
Focks N and Benning C, Plant Physiol 118:91-101, 1998.
Fridborg I et al., *Plant Cell* 11: 1019-1032, 1999.
Geest A H and Hall T C, *Plant Mol Biol* 32(4):579-88, 1996.
Gelvin, S. B., Schilperoort, R. A., Varma, D. P. S., eds. Plant Molecular Biology Manual 1990.
Glick, B R and Thompson, J E, Eds. METHODS IN PLANT MOLECULAR BIOLOGY AND BIOTECHNOLOGY, p. 213-221, CRC Press, 1993.
Harlow E and Lane D, Antibodies: A Laboratory Manual, Cold Spring Harbor Laboratory Press, 1988, New York.
Harlow E and Lane D, Using Antibodies: A Laboratory Manual, Cold Spring Harbor Laboratory Press, 1999, New York
Hayashi H et al., *Science* 258: 1350-1353, 1992.
James D W and Dooner H K (1990) Theor Appl Genet. 80, 241-245.
Jensen, L. G., et al., *Proc. Natl. Acad. Sci. USA* 93:3487-3491, 1996.
Jones J D et al, Transgenic Res 1:285-297 1992.
Kardailsky I et al., *Science* 286: 1962-1965, 1999.
Kline et al., Nature (1987) 327:70.
Kunkel T A et al., *Methods Enzymol.* 204:125-39, 1991.
Lemieux B, et al. 1990, Theor Appl Genet. 80, 234-240.
Nakamura Y et al, 1999, Nucleic Acids Res 27:292.
Napoli, et al, *Plant Cell* 2:279-289, 1990.
Omirulleh et al., Plant Mol. Biol. 21(3):415-28, 1993.
Sambrook et al. Molecular Cloning: A Laboratory Manual (Second Edition), Cold Spring Harbor Press, Plainview, N.Y., 1989.
Schaffer R, et al., *Cell* 93: 1219-1229, 1998.
Sheehy et al., Proc. Natl. Acad. Sci. USA (1988) 85:8805-8809.
Smith, et al., *Nature* 334:724-726, 1988.
Smith et al., Mol. Gen. Genetics (1990) 224:477-481.
Thompson J D et al, 1994, Nucleic Acids Res 22:4673-4680.
van der Krol et al., Biotechniques (1988) 6:958-976.
van der Krol et al., The Plant Cell (1990) 2:291-299.
Van Haaren M J J et al., Plant Mol Bio 21:625-640, 1993.
Verdaguer B et al., Plant Mol Biol 37:1055-1067, 1998.
Waterhouse, et al., *Proc. Natl. Acad. Sci. USA* 95:13959-13964, 1998.
Weigel D, et al., *Plant Physiology*, 122:1003-1013, 2000.
Wilson K et al., *Plant Cell* 8: 659-671, 1996.
Yadav N S et al. (1993) Plant Physiol 103, 467-476.
Bert et al., Theor Appl Genet. 2003 June; 107(1):181-9.
Colbert et al (2001) Plant Physiol 126:480-484.
Jako, et al., Plant Physiology 126(2):861-74, 2001.
Katavic, et al., Plant Physiology, 108(1):399-409, 1995.
Lionneton et al, Genome. 2002 December; 45(6):1203-15).
McCallum et al (2000) Nature Biotechnology 18:455-457).

We claim:

1. A transgenic plant comprising a heterologous polynucleotide that encodes a HIO32.2 polypeptide having an amino acid sequence at least 95% identical to the amino acid sequence of SEQ ID NO: 2 and conveying a high oil phenotype on a plant when expressed in said plant, whereby the transgenic plant has at least 3.5% greater seed oil content relative to a plant of the same species that does not comprise the heterologous polynucleotide.

2. The transgenic plant of claim 1, wherein the heterologous polynucleotide encodes a HIO32.2 polypeptide having the amino acid sequence of SEQ ID NO: 2.

3. The transgenic plant of claim 1, which is selected from the group consisting of rapeseed, soy, corn, sunflower, cotton, cocoa, safflower, oil palm, coconut palm, flax, castor and peanut.

4. The transgenic plant of claim 1, further comprising a heterologous constitutive promoter operatively linked to the heterologous polynucleotide.

5. A plant part obtained from the plant according to claim 1.

6. The plant part of claim 5, wherein the plant part has at least 3.5% greater oil content relative to an equivalent plant part obtained from a plant of the same species that does not comprise the heterologous polynucleotide.

7. A meal, feed, or food comprising a plant part obtained from the plant of claim 1, wherein the meal, feed, or food has at least 3.5% greater oil content relative to meal feed or food comprising a plant part from a plant of the same species that does not comprise the heterologous polynucleotide.

8. The plant part of claim 5, which is a seed.

9. The seed of claim 8, wherein the seed has at least 3.5% greater oil content relative to seed from a plant of the same species that does not comprise the heterologous polynucleotide.

10. A meal, feed, or food comprising the seed of claim 8, wherein the meal, feed, or food has at least 3.5% greater oil content relative to meal, feed, or food comprising seed from a plant of the same species that does not comprise the heterologous polynucleotide.

11. A method of producing oil comprising growing the transgenic plant of claim 1 and recovering oil from said plant.

12. The method of claim 11, wherein the oil is recovered from a seed of the plant.

13. A feed, meal, grain, food, or seed comprising a polypeptide:
   encoded by the nucleic acid sequence as set forth in SEQ ID NO: 1;
   having the amino acid sequence set forth in SEQ ID NO: 2; or
   having an amino acid sequence at least 95% identical to the amino acid sequence of SEQ ID NO: 2, wherein the feed, meal, grain, food, or seed has at least 3.5% greater oil content relative to meal, grain, food, or seed that does not comprise the polypeptide.

14. A transgenic plant with a high oil phenotype made by a method comprising:
   introducing into progenitor cells of the plant a heterologous constitutive promoter operatively linked to a heterologous polynucleotide that encodes a HIO32.2 polypeptide, to produce transformed cells overexpressing the HIO32.2 polypeptide, wherein the HIO32.2 polypeptide has an amino acid sequence at least 95% identical to the amino acid sequence of SEQ ID NO: 2 and conveys a high oil phenotype on a plant when expressed in said plant;
   growing the transformed progenitor cells to produce a transgenic plant; and
   identifying the high oil phenotype in said transgenic plant by measuring oil content of the transgenic plant and selecting a transgenic plant that possesses at least 3.5% greater seed oil content relative to a plant of the same species that does not comprise the heterologous constitutive promoter operatively linked to the heterologous polynucleotide;
   thereby producing the transgenic plant with a high oil phenotype.

15. The transgenic plant of claim 14 wherein the HIO32.2 polypeptide has the amino acid sequence of SEQ ID NO: 2.

* * * * *

UNITED STATES PATENT AND TRADEMARK OFFICE
CERTIFICATE OF CORRECTION

PATENT NO. : 8,168,866 B2  
APPLICATION NO. : 12/427594  
DATED : May 1, 2012  
INVENTOR(S) : Lightner et al.

Page 1 of 1

It is certified that error appears in the above-identified patent and that said Letters Patent is hereby corrected as shown below:

On the Title Page. Item (56) OTHER PUBLICATIONS:

Right column, line 45, "*Genet.*, 80(2):241-245, 1990. Katavic et al.," should read --*Genet.*, 80(2):241-245, 1990. Katavic et al.,--.

In the Specification:

Column 10, line 10, "transformation of in" should read --transformation of--.

Column 10, line 14, "from least" should read --from at least--.

Column 15, line 56, "follows" should read --following--.

Signed and Sealed this  
First Day of April, 2014

Michelle K. Lee  
*Deputy Director of the United States Patent and Trademark Office*

SEQUENCE LISTING

<160> NUMBER OF SEQ ID NOS: 3

<210> SEQ ID NO 1
<211> LENGTH: 279
<212> TYPE: DNA
<213> ORGANISM: Arabidopsis thaliana

<400> SEQUENCE: 1

| | | |
|---|---|---|
| atgtctagca gaaaatcacg ttcaagacaa actggagctt ccatgatcac ggatgaacaa | 60 |
| atcaacgatc ttgtcctcca gcttcatcgg cttctccccg aacttgctaa caacagacgc | 120 |
| tctggaaagg tttcagcatc aagggtatta caagagacat gcagttacat aaggaacttg | 180 |
| agcaaagaag tggatgatct tagtgaaaga ttgtctcaac ttttggaatc aactgattca | 240 |
| gctcaagctg cactaatccg aagtttgctt atgcagtag | 279 |

<210> SEQ ID NO 2
<211> LENGTH: 92
<212> TYPE: PRT
<213> ORGANISM: Arabidopsis thaliana

<400> SEQUENCE: 2

Met Ser Ser Arg Lys Ser Arg Ser Arg Gln Thr Gly Ala Ser Met Ile
1               5                   10                  15

Thr Asp Glu Gln Ile Asn Asp Leu Val Leu Gln Leu His Arg Leu Leu
            20                  25                  30

Pro Glu Leu Ala Asn Asn Arg Arg Ser Gly Lys Val Ser Ala Ser Arg
        35                  40                  45

Val Leu Gln Glu Thr Cys Ser Tyr Ile Arg Asn Leu Ser Lys Glu Val
    50                  55                  60

Asp Asp Leu Ser Glu Arg Leu Ser Gln Leu Leu Glu Ser Thr Asp Ser
65                  70                  75                  80

Ala Gln Ala Ala Leu Ile Arg Ser Leu Leu Met Gln
            85                  90

<210> SEQ ID NO 3
<211> LENGTH: 697
<212> TYPE: DNA
<213> ORGANISM: Arabidopsis thaliana

<400> SEQUENCE: 3

| | | |
|---|---|---|
| gatttctttc tcgatcccca acatcactag ctagctcctt gtacacactc tacaacccca | 60 |
| cctagctaca tcacttaatt agttttacca atttcaaatt ctcacctgtc actagctata | 120 |
| tttcataact gatcattacc aactcatcac tacatattat tggctaggat tcaccattag | 180 |
| acttaagatt agttgattta ttacatatat aagatgtcta gcaggaggtc acggtcaagg | 240 |
| caaacaagta gttcaaggaa tatcaccgat gatcagatca atgatcttgt ctctaagttg | 300 |
| caacagcttc ttccagagat tcgcgatagg cgctctgaca aggtttcagc ttccaaggtg | 360 |
| ttgcaagaga catgcaacta tattagaagc ttacacaggg aagtgggtga cctaagcgag | 420 |
| cgtttatctg agctcctgga tacaactgac acggctcaag ctgcaataat tagaaattta | 480 |
| ctgatgcaat agatcggtgc agttgttaat ttatcgtata attcatagtt aacacttcag | 540 |
| tacttgtgaa ccgatccagt cactggtcgt gtatttctta ttctcttttc gtttcacttt | 600 |
| tttttttttt tttgtgctgg ttcttgtcca ctaatatgaa tgattactgc ttttgcaaag | 660 |
| cccaatttcc ttatatatta aataaaagtt tcagagg | 697 |